United States Patent
Pfahnl et al.

(10) Patent No.: US 10,099,244 B2
(45) Date of Patent: Oct. 16, 2018

(54) DISPENSING AND ASPIRATING SYSTEM INCLUDING A SYRINGE HOLDING AND ACTUATION DEVICE

(71) Applicant: PDAP, LLC, Eden Prarie, MN (US)

(72) Inventors: Andreas Carl Pfahnl, Eden Prairie, MN (US); Patrick Ryan Corneille, San Francisco, CA (US); Robert D. Carter, Apple Valley, MN (US); Anil C. Asrani, Plymouth, MN (US)

(73) Assignee: PDAP, LLC, Eden Prairie, MN (US)

( * ) Notice: Subject to any disclaimer, the term of this patent is extended or adjusted under 35 U.S.C. 154(b) by 622 days.

(21) Appl. No.: 14/419,439

(22) PCT Filed: Aug. 2, 2013

(86) PCT No.: PCT/US2013/053368
§ 371 (c)(1),
(2) Date: Feb. 3, 2015

(87) PCT Pub. No.: WO2014/022750
PCT Pub. Date: Feb. 6, 2014

(65) Prior Publication Data
US 2015/0209821 A1  Jul. 30, 2015

Related U.S. Application Data

(60) Provisional application No. 61/679,289, filed on Aug. 3, 2012.

(51) Int. Cl.
*B05C 17/00* (2006.01)
*B05C 17/01* (2006.01)
(Continued)

(52) U.S. Cl.
CPC ......... *B05C 17/0123* (2013.01); *A61M 1/007* (2014.02); *A61M 1/0064* (2013.01);
(Continued)

(58) Field of Classification Search
CPC .... A61B 17/00491; A61B 2017/00407; A61B 2017/2943; A61M 1/0064; A61M 1/007;
(Continued)

(56) References Cited

U.S. PATENT DOCUMENTS

| 1,718,596 | A |   | 6/1929 | Smith |
| 2,892,457 | A | * | 6/1959 | Sturtz ................. A61M 5/00 222/391 |

(Continued)

FOREIGN PATENT DOCUMENTS

WO    WO 02/094343    11/2002

*Primary Examiner* — Brandy S Lee
(74) *Attorney, Agent, or Firm* — Kagan Binder, PLLC

(57) ABSTRACT

The present invention provides actuation mechanisms that incorporate a transmission assembly that allows the mechanisms to cause actuation of workpieces according to a plurality of transmission modes (e.g., at least one forward transmission mode and at least one reverse transmission mode) on demand. Motion, direction, and/or force can be controlled by selecting the corresponding transmission mode. The mechanisms preferably are trigger-actuated by hand (i.e., manually) to cause movement of a workpiece in a desired direction. Desired directions can be linear or nonlinear. The same hand used for trigger action can also be used to change transmission modes in many modes of practice, even while using substantially the same grip used for trigger actuation. In other instances, actuation can be automated rather than manual. Preferably, both actuation and witching among transmission modes can be accomplished with one hand, even while maintaining substantially the same grip that is used for actuation.

13 Claims, 12 Drawing Sheets

(51) Int. Cl.

| | | |
|---|---|---|
| *A61M 5/00* | (2006.01) | |
| *A61M 5/145* | (2006.01) | |
| *A61M 1/00* | (2006.01) | |
| *A61M 3/02* | (2006.01) | |
| *A61M 5/31* | (2006.01) | |
| *A61M 5/315* | (2006.01) | |
| *A61B 17/00* | (2006.01) | |
| *A61B 17/29* | (2006.01) | |

(52) U.S. Cl.
CPC .......... *A61M 3/0262* (2013.01); *A61M 5/007* (2013.01); *A61M 5/1452* (2013.01); *A61M 5/3148* (2013.01); *A61M 5/31586* (2013.01); *B05C 17/0116* (2013.01); *A61B 17/00491* (2013.01); *A61B 2017/00407* (2013.01); *A61B 2017/2943* (2013.01); *A61M 5/31581* (2013.01); *A61M 2005/14506* (2013.01); *A61M 2005/3114* (2013.01); *A61M 2005/3152* (2013.01)

(58) Field of Classification Search
CPC ........... A61M 2005/14506; A61M 2005/3114; A61M 2005/3152; A61M 3/0262; A61M 5/007; A61M 5/1452; A61M 5/3148; A61M 5/31581; A61M 5/31586; B05C 17/0116; B05C 17/0123
See application file for complete search history.

(56) References Cited

U.S. PATENT DOCUMENTS

| | | | |
|---|---|---|---|
| 4,516,969 | A | 5/1985 | Kintner |
| 4,737,151 | A | 4/1988 | Clement et al. |
| 4,926,722 | A | 5/1990 | Sorensen et al. |
| 5,009,134 | A | 4/1991 | Sorensen et al. |
| 5,057,078 | A | 10/1991 | Foote et al. |
| 5,078,690 | A | 1/1992 | Ryan |
| D337,821 | S | 7/1993 | Tan |
| 5,469,860 | A | 11/1995 | De Santis |
| 5,696,726 | A | 12/1997 | Tsukikawa |
| 6,722,232 | B1 * | 4/2004 | Day ..................... B25B 13/467 81/56 |
| 7,325,797 | B2 | 2/2008 | Kloepfer et al. |
| D576,273 | S | 9/2008 | McClintok et al. |
| 7,757,904 | B2 | 7/2010 | Rumrill et al. |
| 7,967,793 | B2 | 6/2011 | Sibbitt, Jr. et al. |
| 8,074,340 | B2 | 12/2011 | Cicenas et al. |

* cited by examiner

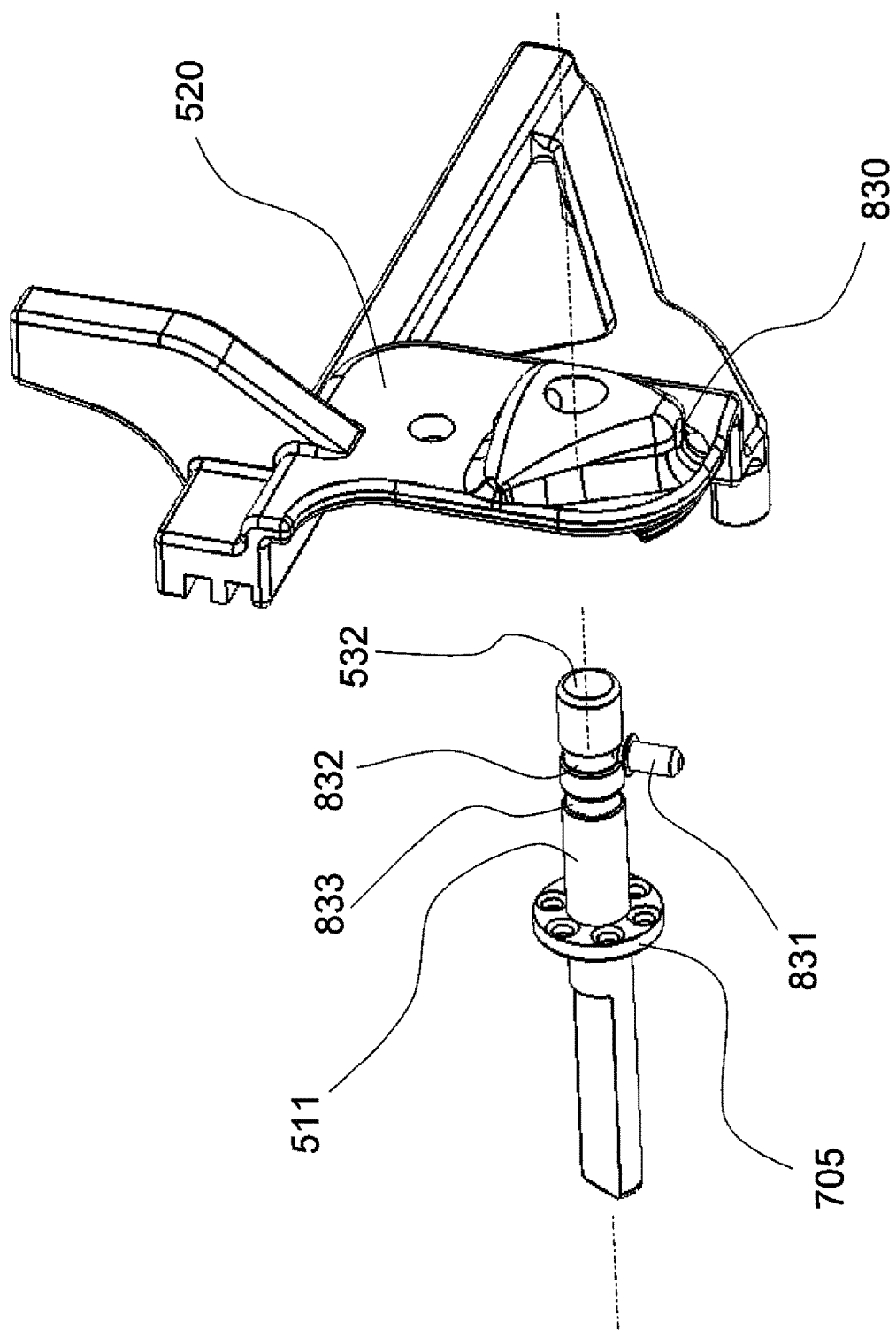

DISPENSING AND ASPIRATING SYSTEM INCLUDING A SYRINGE HOLDING AND ACTUATION DEVICE

STATEMENT OF PRIORITY

The present patent application claims priority to International Application No. PCT/US2013/053368, filed Aug. 2, 2013, which in turns claims priority under 35 USC § 119(e) from United States Provisional patent application having Ser. No. 61/679,289, filed on Aug. 3, 2012, by Pfahnl et al. and entitled DISPENSING AND ASPIRATING SYSTEM INCLUDING A SYRINGE HOLDING AND ACTUATION DEVICE, wherein the disclosures of these applications are incorporated herein by reference in their respective entireties for all purposes.

FIELD OF THE INVENTION

The invention relates generally to systems and methods for controlling the motion of two elements using a compact transmission whose modes of actuation can be easily selected on demand. An example application of the invention includes injecting and/or aspirating fluids using a syringe in combination with a syringe holding and actuation device. More specifically, the present invention relates to such systems and methods in which a holding and actuation device includes a compact transmission to allow a user to easily select the direction of the motion, e.g., an actuating mechanism can be moved forward or in reverse on demand. In the case of fluid delivery, it is possible to switch between the aspiration or dispensing modes of function on demand.

BACKGROUND OF THE INVENTION

Syringes are available in a variety of sizes and are intended to dispense (inject) as well aspirate (extract) a variety of substances, most often fluids but also dispersions, gels, solids such as powders, or gases. Syringes are used to inject or aspirate fluid in several therapeutic and diagnostic medical procedures such as the following illustrative examples:
1) Centesis Procedures—including Thoracentesis (removal and optional analysis of fluid in the chest, Paracentesis (removal and optional analysis of fluid in the abdomen), Pericardialcentesis (removal and optional analysis of fluid from the pericardial space around the heart), and Arthrocentesis (removal and optional analysis of fluid from a joint).
2) Abscess Aspiration—removal and optional analysis of fluid collection sites common in the body particularly the breast, brain or kidneys.
3) Contrast Media Injection—special fluid to better visualize blood vessels for cardiology procedures. Aspiration is used to verify the needle puncture into a vasculature, and injection is used to deliver the contrast media into the vasculature.
4) Exchange Transfusions—including slow and careful replacement of blood for adult and pediatric blood diseases.
5) Surgical Wound Irrigation—including high velocity cleansing of traumatic injuries. A syringe aspirates saline, for example, from a reservoir and irrigates a wound site.

The nature of these procedures typically involves extensive manipulation of the syringe and stabilization of the injection/aspiration site. These tasks are more difficult with high viscosity fluids and/or larger syringes.

Syringes can be manually operated with one or two hands, can be manually operated with the assistance of a holding/actuation accessory, or can be used with a variety of automatic devices which aide in controlling the movement of the substance within the syringe. Automation comes with additional cost, size, and maintenance disadvantages compared to manual activation.

Larger size syringes, such as 60 mL ones, are common and well-suited for many procedures. However, larger sized syringes are more challenging to use manually with one hand, even when used in combination with conventional actuation accessories. This difficulty could compromise patient safety, delivery and aspiration accuracy, and/or extend procedure times. Having a second person assist in helping resolve these issues increases procedure cost.

Syringe accessories in the form of hand pieces or devices have been described and developed that address some of the challenges associated with using syringes to accomplish aspiration. A handheld device used with syringes to provide aspiration function is depicted in patents such as U.S. Pat. No. 5,469,860 and USD337821. A commercially available device is available from Inrad, Inc. (Kentwood, Mich.) under the trade designation Aspiration Biopsy Syringe Gun. Several devices also have been described that are used with syringes to dispense syringe contents. See, e.g., USD576273.

Some syringes include features to assist with single handed aspiration. These features include loops or rings to facilitate finger and thumb action. These features can facilitate both dispensing and aspiration. Several variations of an early control syringe exist. See, e.g., U.S. Pat. No. 4,516,969.

Commercially available devices with trigger-actuated ratchet mechanisms are used in so-called caulk guns for dispensing adhesives and caulking materials from prefilled cartridges. The guns and cartridges are available in different sizes. Illustrative products are and manufactured by companies such as 3M Co. (St. Paul, Minn.) and Henkel Corp. (Rocky Hill, Conn.). A recent patent US7757904B2 is an example of such a device for caulk cartridges.

Commercially available bar clamping devices exist that utilize ratchet mechanism principles. Examples are US8074340B2 and U.S. Pat. No. 4,926,722. Some of these clamps can be reconfigured to a spreading bar clamp as described in U.S. Pat. No. 5,009,134. These devices illustrate how high forces can be used to create a clamping or spreading motion. A bar clamp that uses a switching mechanism to select between clamping and spreading functions is described in US7325797B2. A third example device is marketed by Avanca Medical Devices, Inc and described in US7967793B2. This device allows the dispensing and aspiration of a syringe with a single hand. A fourth example is a balloon inflation device that utilizes a threaded plunger that is rotated clockwise or counterclockwise to advance or retract the plunger of a syringe. See, e.g., U.S. Pat. No. 5,057,078.

There are other applications where it is desired to have an ability to control motion of one or more components and the direction of such motion. Some additional applications involve controlling the motion of a fluid (e.g., to dispense, inject, or aspirate a fluid). Other applications involve controlling the position of one or more solid items.

Many conventional designs can limit or impede a user from dispensing and aspirating syringes, particularly large sized ones with one hand when one hand operation is desired. Therefore, in light of these challenges, it is desired to have a compact and lightweight device that can provide easy dispensing and aspirating modes when used with a syringe, the ability to switch between the two modes and do all this with one hand if desired without requiring outside assistance or requiring setting the syringe down at any point. It is also desirable that the device be able to provide mechanical advantage so that the user-applied force can be leveraged for very high dispensing or aspiration forces. It also is desired that the device be MRI safe and compatible, since therapeutic and diagnostic procedures using syringes may be conducted under Magnetic Resonance Imaging (MRI).

SUMMARY

The present invention provides actuation mechanisms that incorporate a transmission assembly that allows the mechanisms to cause actuation in a plurality of transmission modes (e.g, at least one forward transmission mode and at least one reverse transmission mode). The mechanisms preferably are trigger-actuated by hand (i.e., manually) to cause movement of a workpiece in a desired direction. Desired directions can be linear or nonlinear. The same hand used for trigger action can also be used to change transmission modes in many modes of practice, even while using substantially the same grip used for trigger actuation. In other instances, actuation can be automated rather than manual. The transmission assembly is compact, elegantly simple in design, easy to manufacture and assemble, and easy to use (even with one hand if desired) to switch between transmission modes on demand. The actuation mechanism is useful in any application in which it is desired to move a workpiece, which can be a solid, liquid, or gas, in multiple directions, e.g., forward and reverse, gripping and releasing, etc. Exemplary uses include actuating syringes, actuating caulk cartridges, actuating mechanical clamps, actuating vacuum gripping devices, actuating furniture componentry to change the configuration of furniture (e.g., raising and lowering the height of a chair seat or changing the angle of a desk top), actuating toy water guns, actuating spray containers, and the like.

For example, the present invention provides systems and methods in which a syringe actuation device is coupled to and then used with a syringe to aspirate or dispense, on demand, the syringe. In preferred modes, trigger actuation is used to operate the syringe. Using the transmission assembly to select the desired transmission mode, the same trigger action can be used both to dispense and aspirate syringe contents as desired. Advantageously, actuation and switching between dispensing and aspiration modes can be accomplished with one hand. In illustrative embodiments, the actuation devices of the present invention include a configurable transmission assembly that couples an actuation force to different motions of a syringe carriage. In one mode, the carriage actuates the syringe in a dispensing mode in which syringe contents are dispensed. In another mode, the carriage actuates the syringe in an aspiration mode to draw material into the syringe.

The present invention offers numerous advantages over other syringe dispensing and aspiration devices. In many embodiments, the devices are made of materials that allow the devices to be used in diverse environments including with Magnetic Resonance Imaging equipment. For example, representative embodiments can be made of non ferrous materials including plastics that are suitable for use in procedures that also involve use of Magnetic Resonance Imaging equipment, which creates a strong magnetic field around the patient.

Preferred embodiments allow, if desired, single-handed aspiration and dispensing of even very large syringes that otherwise would have a large plunger stroke or require much actuation force. Furthermore, an ergonomically designed and placed clutch of a configurable transmission system allows the same hand performing the aspiration and dispensing to also switch between these two modes without requiring a second hand or having to set the device down. Other preferred embodiments may remove or add features of the clutch and configurable transmission system to create aspiration only versions of the invention, or dispensing only versions, or ones with a neutral position (neither aspirating or dispensing).

In one aspect, the present invention relates to a syringe actuation system, comprising:
  a) a syringe comprising a plunger and a syringe body having a first open end and a second open end, wherein the plunger fits into the first open end of the syringe body and is slideable to be moved into the syringe body toward the second open end and is slideable to be pulled from the syringe body away from the second open end; and
  b) a syringe holding and actuation device
    i. a first portion that holds the plunger;
    ii. a second portion that holds the syringe body, wherein the first and second portions are moveable relative to each other such that the plunger can be moved into and pulled from the syringe body;
    iii. an actuation mechanism coupled to at least one of the first and second portions, wherein actuation of the mechanism causes relative motion between the first and second portions; and
    iv. a transmission coupled to at least one of the first and second portions and to the actuation mechanism, said transmission comprising:
      1. a first transmission mode that causes relative movement of the first and second portions in a manner effective to cause the plunger to be moved into the syringe body when the actuation mechanism is actuated;
      2. a second transmission mode that causes relative movement of the first and second portions to cause the plunger to be pulled from the syringe body when the actuation mechanism is actuated; and
      3. a clutch system comprising a first configuration that causes the transmission to be in the first transmission mode and a second configuration that causes the transmission to be in the second transmission mode, wherein the clutch system comprises a rotatable shaft having an axis of rotation, wherein rotation of the shaft causes relative movement of the first and second portions in the first and second transmission modes, and wherein the shaft is shiftable along the axis of shaft rotation in a manner such that shifting the shaft along the axis of shaft rotation shifts the transmission between the first and second transmission modes on demand.

In another aspect, the present invention relates to a syringe holding and actuation device for actuation of a syringe comprising a syringe body and a plunger, said device comprising:
  a) a first portion that holds the plunger;

b) a second portion that holds the syringe body, wherein the first and second portions are moveable relative to each other such that the plunger can be moved into and pulled from the syringe body;

c) an actuation mechanism coupled to at least one of the first and second portions, wherein actuation of the mechanism causes relative motion between the first and second portions; and d) a transmission coupled to at least one of the first and second portions and to the actuation mechanism, said transmission comprising:
   i. a first transmission mode that causes relative movement of the first and second portions in a manner effective to cause the plunger to be moved into the syringe body when the actuation mechanism is actuated;
   ii. a second transmission mode that causes relative movement of the first and second portions to cause the plunger to be pulled from the syringe body when the actuation mechanism is actuated; and
   iii. a clutch system comprising a first configuration that causes the transmission to be in the first transmission mode and a second configuration that causes the transmission to be in the second transmission mode, wherein the clutch system comprises a rotatable shaft having an axis of rotation, wherein rotation of the shaft causes relative movement of the first and second portions in the first and second transmission modes, and wherein the shaft is shiftable along the axis of shaft rotation in a manner such that shifting the shaft along the axis of shaft rotation shifts the transmission between the first and second transmission modes on demand.

In another aspect, the present invention relates to a method of actuating a syringe, comprising the steps of:
   a) providing a syringe actuation device according to claim 2;
   b) loading a syringe into the device;
   c) selecting a mode of actuation selected from dispensing and aspiration;
   d) causing the actuation device to be in the desired mode of actuation; and
   e) actuating the device to cause corresponding actuation of the syringe.

In another aspect, the present invention relates to a syringe holding and actuation device for actuation of a syringe comprising a syringe body and a plunger, said device comprising:
   a) a first portion comprising (i) a slideable carriage that holds the plunger and (ii) gear teeth provided along at least a portion of the slideable carriage such that rotational motion applied to said gear teeth causes generally linear translation of the carriage back and forth corresponding to the direction of the applied rotational motion;
   b) a second portion that holds the syringe body, wherein the carriage is slideably attached to the second portion such that the carriage is linearly translatable relative to the second portion such that the plunger held by the carriage can be moved into and pulled from the syringe body held by the second portion as the carriage translates;
   c) an actuation mechanism coupled to at least one of the first and second portions, wherein actuation of the mechanism causes linear translation of the carriage relative to the second portion; and
   d) a transmission mounted in the second portion and coupled to the translatable carriage, said transmission comprising:
      i. a rotatably driven gear coupled to the gear teeth of the carriage, said rotatably driven gear being driveable in first and second rotational directions to cause corresponding linear translation of the carriage in first and second linear directions relative to the second portion;
      ii. a first selectively driven gear rotationally coupled to the rotatably driven gear in a manner effective to cause rotation of the rotatably driven gear in the first rotational direction when the first selectively driven gear is selectively driven;
      iii. a second selectively driven gear rotationally coupled to the rotatably driven gear in a manner effective to cause rotation of the rotatably driven gear in the second rotational direction when the second selectively driven gear is selectively driven;
      iv. a clutch system comprising a first configuration that causes the transmission to be in a first transmission mode that selectively drives the first selectively driven gear and a second configuration that causes the transmission to be in a second transmission mode that selectively drives the second selectively driven gear, wherein the clutch system comprises a rotatable shaft having an axis of rotation, wherein the rotatable shaft is rotatably driven by actuation of the actuation mechanism, wherein rotation of the shaft rotatably drives one of the first and second selectively driven gears on demand, and wherein the shaft is shiftable along the axis of shaft rotation in a manner such that shifting the shaft along the axis of shaft rotation shifts the transmission between the first and second transmission modes on demand.

In another aspect, the present invention relates to an actuation device to control motion of a workpiece, comprising:
   a) a moveable component coupled to the workpiece;
   b) a transmission coupled to the moveable component, said transmission comprising:
      i. a first transmission mode that causes the moveable component to be actuated in a first manner when the actuation device is actuated;
      ii. a second transmission mode that causes the moveable component to be actuated in a second manner when the actuation device is actuated; and
      iii. a clutch system comprising a first configuration that causes the transmission to be in the first transmission mode and a second configuration that causes the transmission to be in the second transmission mode, wherein the clutch system comprises a rotatable shaft having an axis of rotation, wherein rotation of the shaft causes the transmission to actuate the moveable component, and wherein the rotatable shaft is shiftable along the axis of shaft rotation in a manner such that shifting the shaft along the axis of shaft rotation shifts the transmission into the first or second transmission modes on demand.

In another aspect, the present invention relates to an actuation device to control motion of a workpiece, comprising:
   a) a moveable component coupled to the workpiece;
   b) a transmission coupled to the moveable component, said transmission comprising:
      i. a rotatably driven gear coupled to the moveable component, said rotatably driven gear being driveable in first and second rotational directions to cause corresponding first and second motions of the moveable component;

ii. a first selectively driven gear rotationally coupled to the rotatably driven gear in a manner effective to cause rotation of the rotatably driven gear in a first rotational direction when the first selectively driven gear is selectively driven;

iii. a second selectively driven gear rotationally coupled to the rotatably driven gear in a manner effective to cause rotation of the rotatably driven gear in a second rotational direction; and iv. a clutch system comprising a first configuration that causes the transmission to be in a first transmission mode that selectively drives the first selectively driven gear and a second configuration that causes the transmission to be in a second transmission mode that selectively drives the second selectively driven gear, wherein the clutch system comprises a rotatable shaft having an axis of rotation, wherein the rotatable shaft is rotatably driven and wherein rotation of the shaft rotatably drives one of the first and second selectively driven gears on demand, and wherein the shaft is shiftable along the axis of shaft rotation in a manner such that shifting the shaft along the axis of shaft rotation shifts the transmission between the first and second transmission modes on demand.

BRIEF DESCRIPTION OF THE DRAWINGS

The accompanying drawings, which are incorporated in and constitute a part of this disclosure, illustrate several aspects of the present invention and together with description of the exemplary embodiment serve to explain the principles of the invention. Additionally, foregoing and other objects, features and advantage of the invention will be apparent from the following description of preferred embodiments of the invention, as illustrated in the accompanying drawings in which like reference characters refer to the same parts throughout the different views. The drawings are not necessarily to scale, emphasis instead being placed upon illustrating the principles of the invention. A brief description of the drawing is as follows:

FIG. 12 is a perspective view of select components of the clutch mechanism of the device of FIG. 5.

DETAILED DESCRIPTION OF THE INVENTION

Exemplary embodiments of the present invention are described in the following with reference to the drawings. It should be understood that such embodiments are by way of example only and merely illustrative of the many possible embodiments which can represent applications of the principles of the present invention. Various changes and modifications obvious to one skilled in the art to which the present invention pertains are deemed to be within the spirit, scope and contemplation of the present invention as further defined in the appended claims. The exemplary embodiments of the present invention described herein are not intended to be exhaustive or to limit the present invention to the precise forms disclosed in the following detailed description. Rather the exemplary embodiments described herein are chosen and described so those skilled in the art can appreciate and understand the principles and practices of the present invention.

Figure 1:
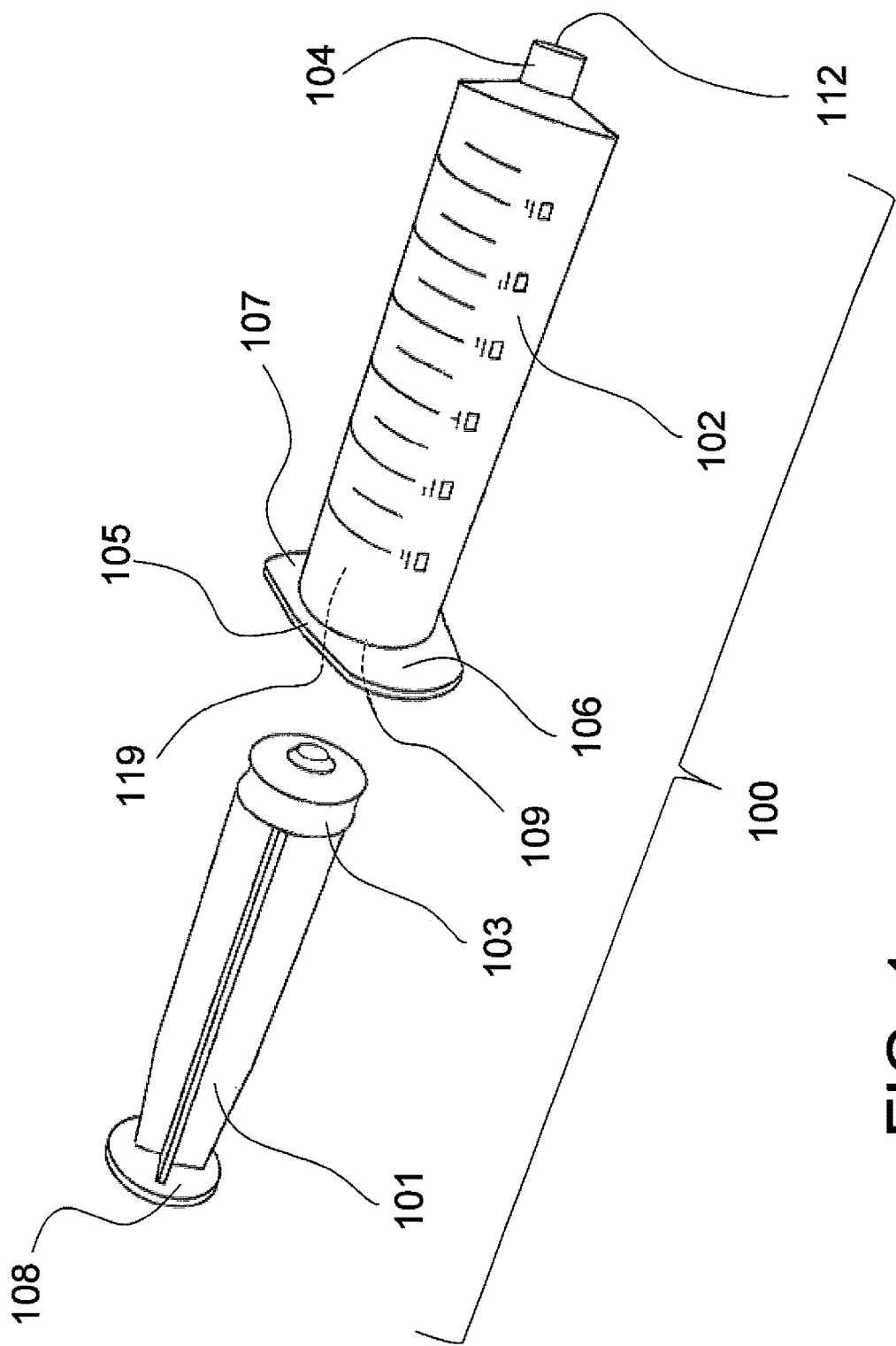
FIG. 1 (prior art) is a perspective view of a typical syringe with the plunger separated from the syringe body.
Figure 2:
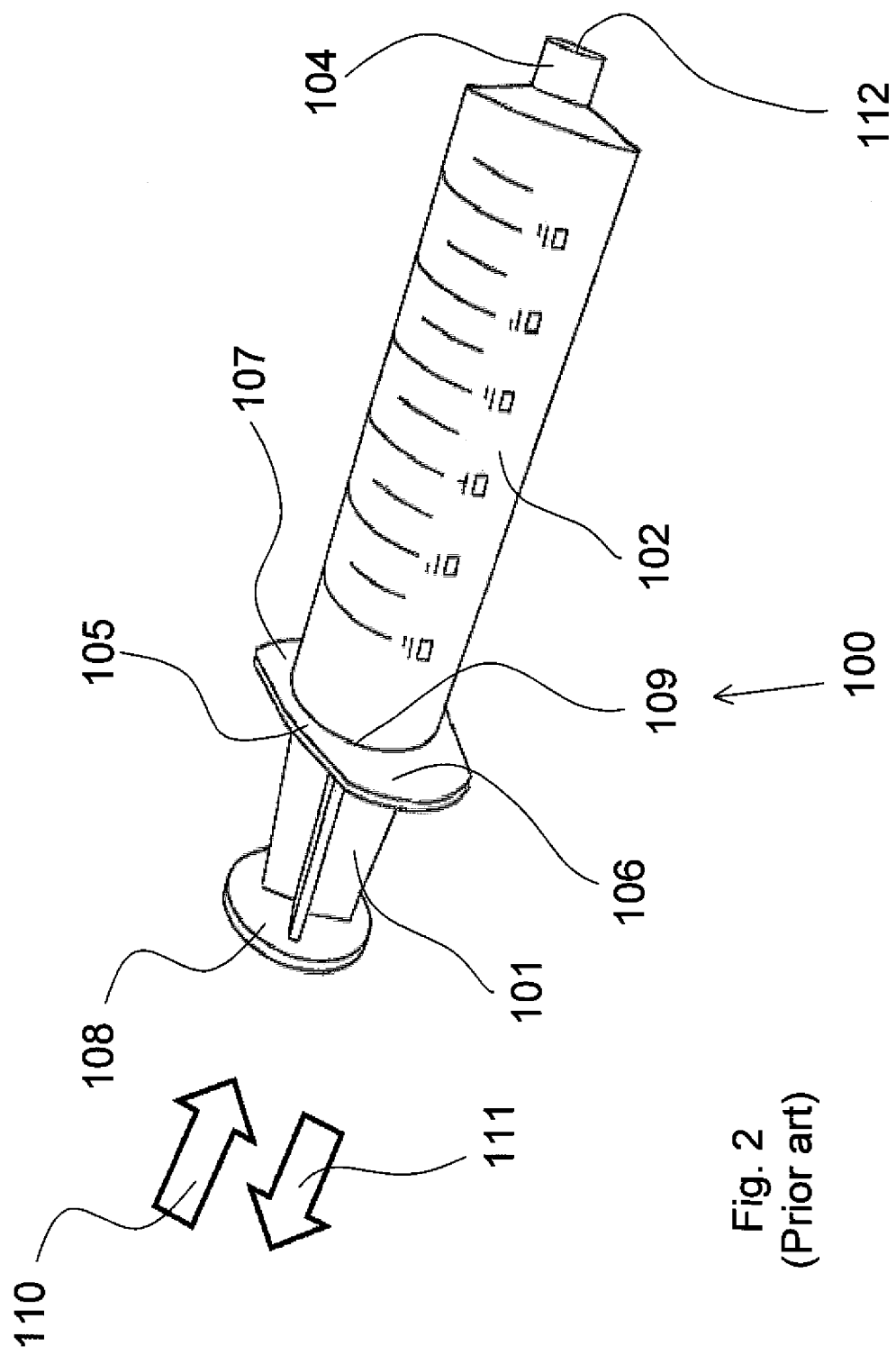
FIG. 2 (prior art) is a perspective view of the syringe of FIG. 1 with the plunger assembled in the syringe body.

Referring to FIGS. 1 and 2, a typical syringe 100 is shown disassembled in FIG. 1 and assembled in FIG. 2. Syringe 100 is a type of syringe that is easily used in many modes of practice of the present invention. One illustrative system of the present invention that incorporates these types of syringes is described further below. The syringe 100 includes a plunger 101 and a syringe body 102. The end of the plunger often is made of a material and of a diameter that allow end 103 and optionally other portion(s) of plunger 101 to seal against the inner wall of the main part of the syringe body 102 along which the plunger 101 moves. Syringe body 102 defines a reservoir 119 for holding material(s) (not shown) to be dispensed from or aspirated into body 102. The open tip 104 of the syringe body 102 is opposite the end 109 through which the plunger 101 is inserted. Tip 104 has an opening 112 through which the fluid passes into and out of the syringe body 102 as the plunger 101 is moved accordingly. This opening 112 is typically smaller than the main portion or bore of the syringe body 102 along which the plunger 101 including 103 travels so that tip 104 can be connected to other components like needles, tubing, and catheters, for example. The exterior of the syringe body 102 typically has a flange 105 to facilitate a user or equipment to interface with the syringe body. In FIG. 1, flange 105 is shown with two extensions or tabs 106 and 107. The plunger 101 typically also has a plunger flange 108 that is used to facilitate a user or equipment to interface with the plunger 101.

The process of injecting or dispensing material that may be within reservoir 119 of the syringe body 102 is accomplished by moving the plunger 101 towards the tip 104 of syringe body 102 as indicated by arrow 110 in FIG. 2. For purposes of the present invention, this first mode of actuation of plunger 101 is referred to as the forward or dispensing mode of actuation. The process of aspirating material into the syringe body 102 is accomplished by moving the plunger 101 away from the tip 104 of the syringe body 102 as indicated by arrow 111 in FIG. 2. For purposes of the present invention, this second mode of actuation of plunger 101 is referred to as the reverse or aspirating mode of actuation. Using syringe 100 by itself, injection and aspiration can be done manually by a user with a single hand if the syringe is not too large. Manual actuation, particularly one-handed actuation, is more difficult with larger syringes. In contrast, manual actuation is substantially easier using principles of the present invention, even with larger syringes. Moreover, the systems of the present invention described below also allow a user to easily select either the forward or reverse actuation modes on demand. In preferred modes of practice, the same hand that actuates the system also can be used to select the desired actuation mode.

Figure 3:
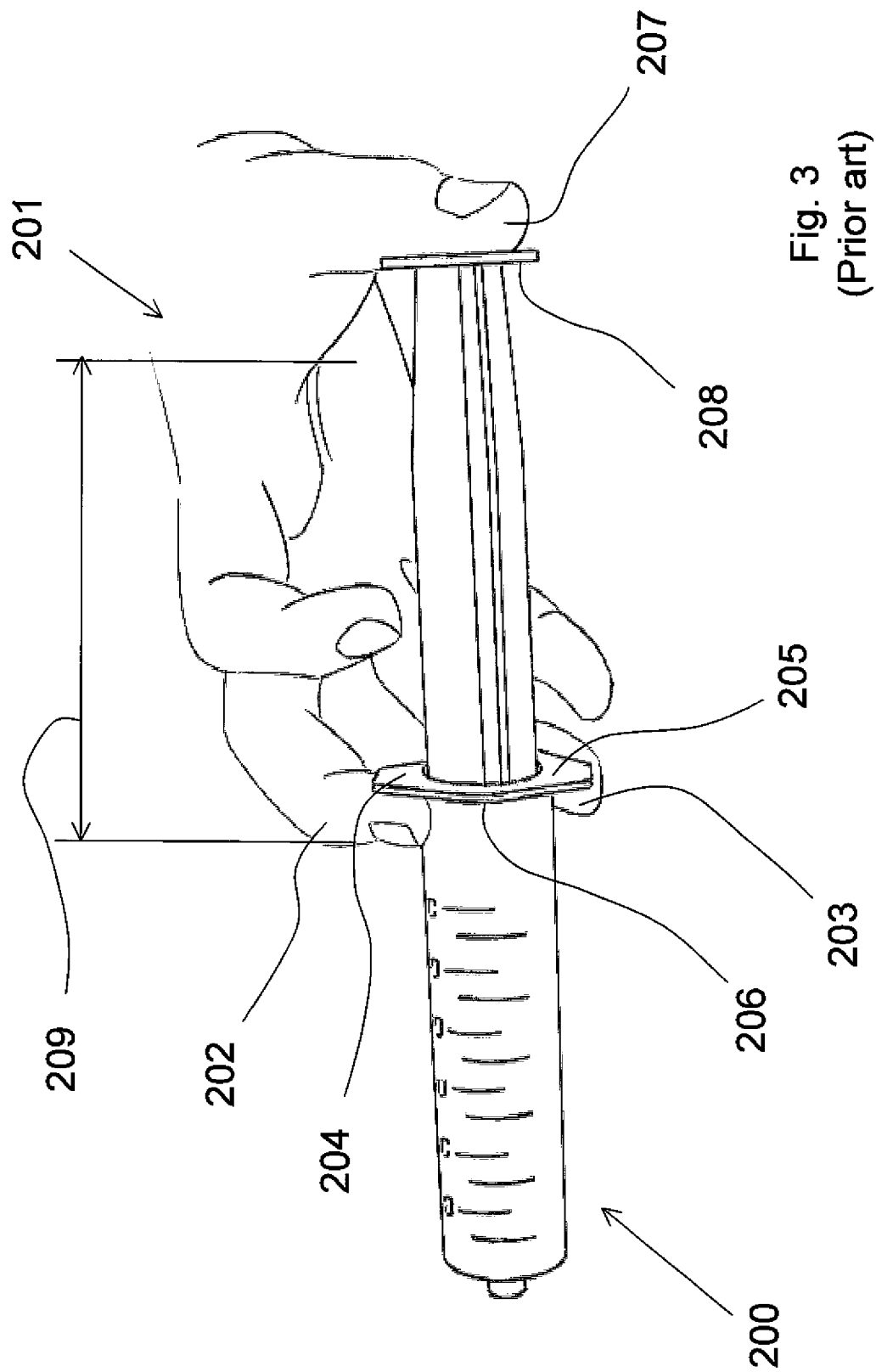
FIG. 3 (prior art) is a perspective view of the syringe of FIG. 1 with a user hand gripping the syringe to dispense or inject.

FIG. 3 illustrates one manner in which a user would hold a syringe 200 for dispensing with a single hand 201 without assistance from an actuation accessory of the present invention. In this example, two fingers 202 and 203 are placed on the tabs 204 and 205 of the syringe body flange 206, and the thumb 207 on the plunger flange 208. When the syringe 200 gets larger in length and cross section size, such as with a 60 mL size syringe, the ability to squeeze a fully filled syringe with a single hand becomes very difficult. One factor contributing to this difficulty is the increasing distance 209 that the fingers 202 and 203 must reach. As this distance 209 approaches the maximum reach of the hand 201, the squeeze force a user can apply decreases. For users with small hands, the distance 209 may be so large that a user may not even be able to reach between the plunger flange 206 and the syringe body flange 208 with one hand to start dispensing.

Figure 4:
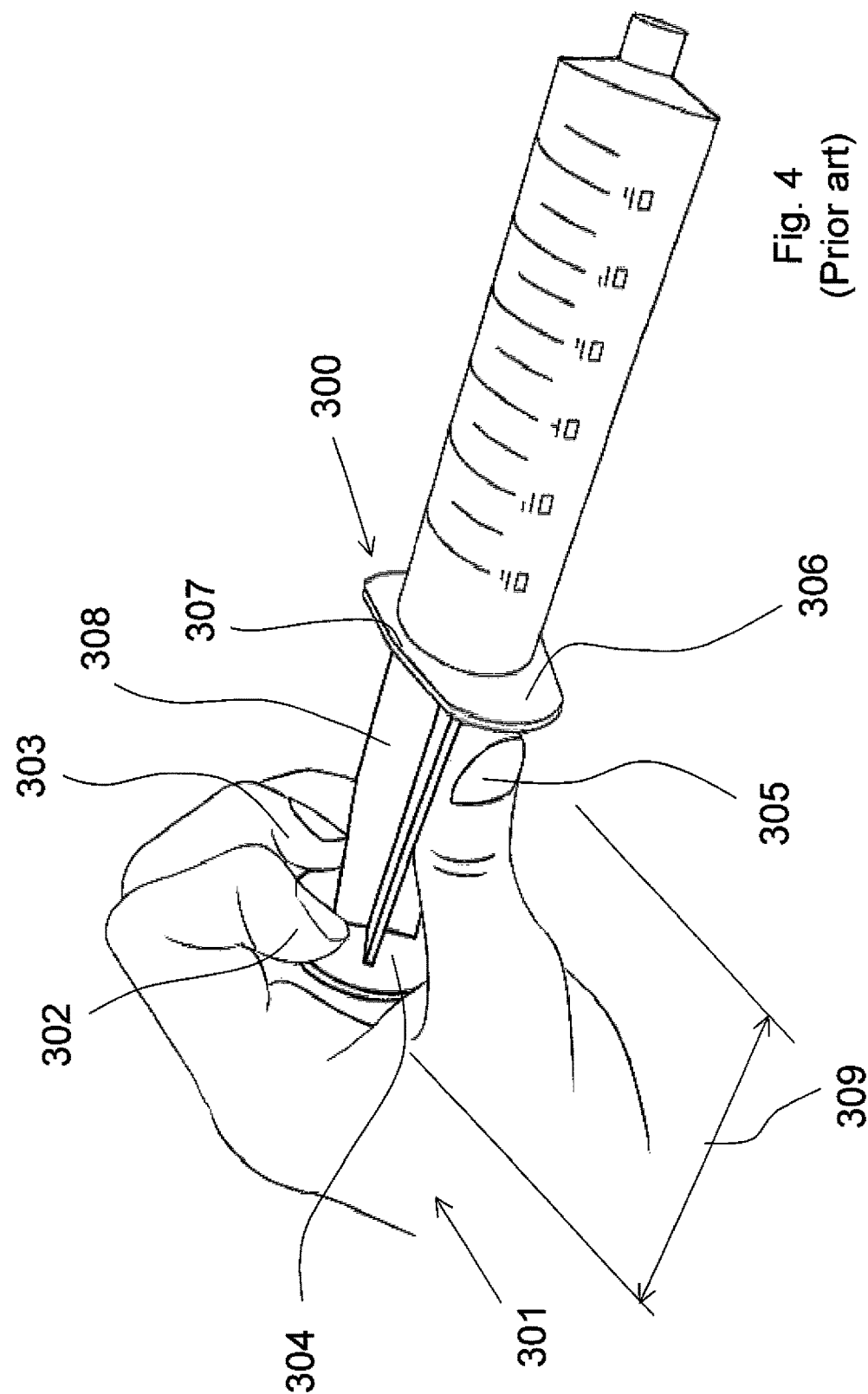
FIG. 4 (prior art) is a perspective view of the syringe of FIG. 1 with a user hand gripping the syringe to aspirate.

FIG. 4 illustrates one manner in which a user would hold a syringe 300 for aspirating with a single hand 301 without assistance from an actuation accessory of the present invention. In this example, two fingers 302 and 303 are placed on the plunger flange 304, and the thumb 305 pushes on one of the tabs 306 of the syringe body flange 307. If the syringe 300 were to be larger in length and cross section size, such as with a 60 mL size syringe, the ability to fully extend the plunger 308 with a single hand becomes very difficult due to the increasing distance 309 that the fingers 302 and 303 must reach. As this distance 309 approaches the maximum reach of the hand 301, the pushing force a user can apply decreases. But even more significant is that the reach is largely limited by the reach of the thumb finger 305 relative to fingers 302 and 303. In some cases, a user may not even be able to fully extend the plunger 308 to completely fill the syringe 300 using only one hand.

FIGS. 3 and 4 illustrate single hand positions holding a relatively large syringe for dispensing and aspiration, respectively. It can be seen that these two hand positions are very different. To switch between the two holds is awkward and cumbersome without setting the syringe down between the holds or without assistance from a second hand. There are other methods in which the syringe can be held with one hand that are not shown. However, in any position, the hand must span both the syringe flange as well as the plunger flange, and, therefore, the stroke is limited by the size of the user's hand.

Figure 5:
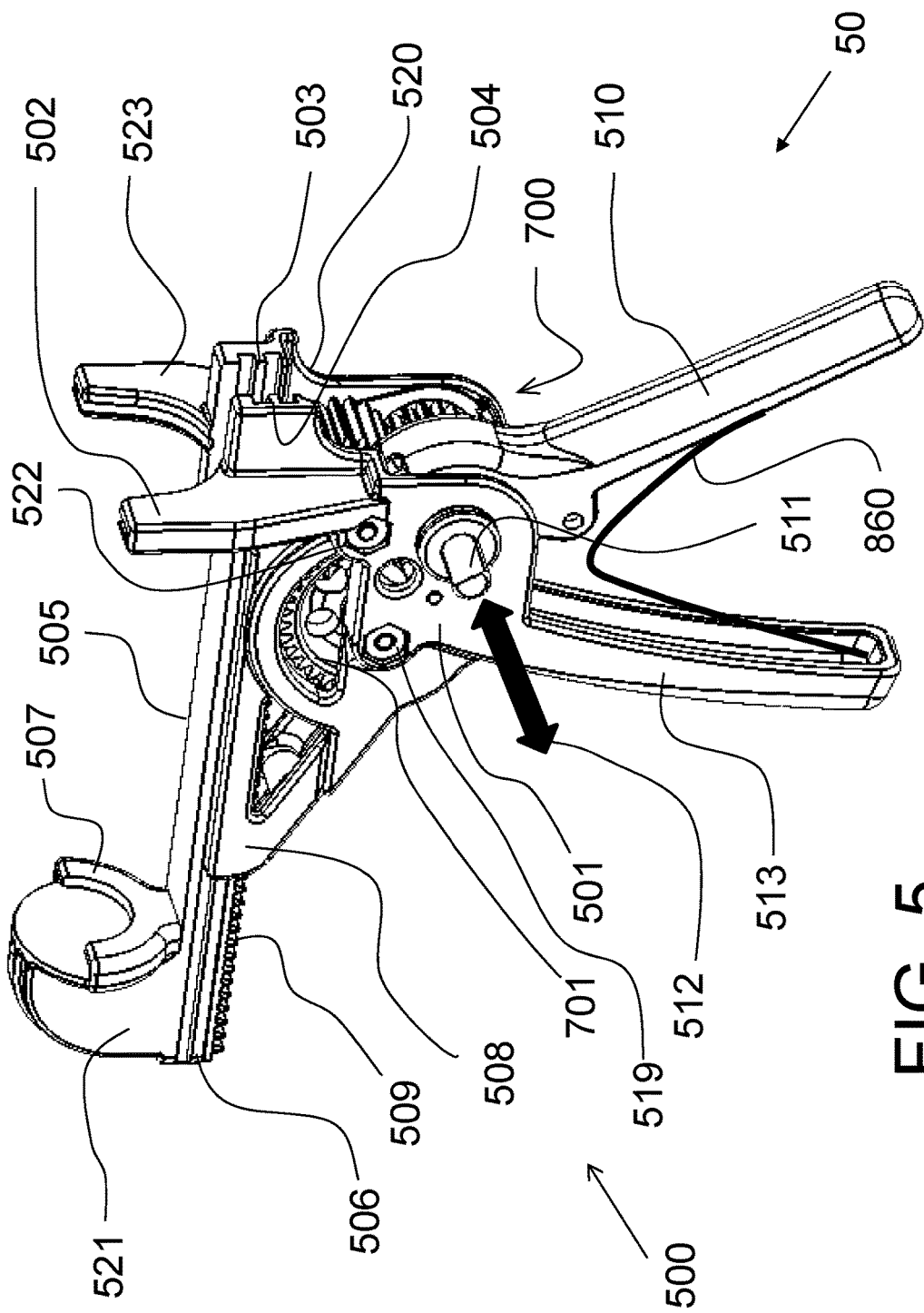
FIG. 5 is a perspective view of a preferred embodiment of an injection and aspiration device according to the present invention.
Figure 6:
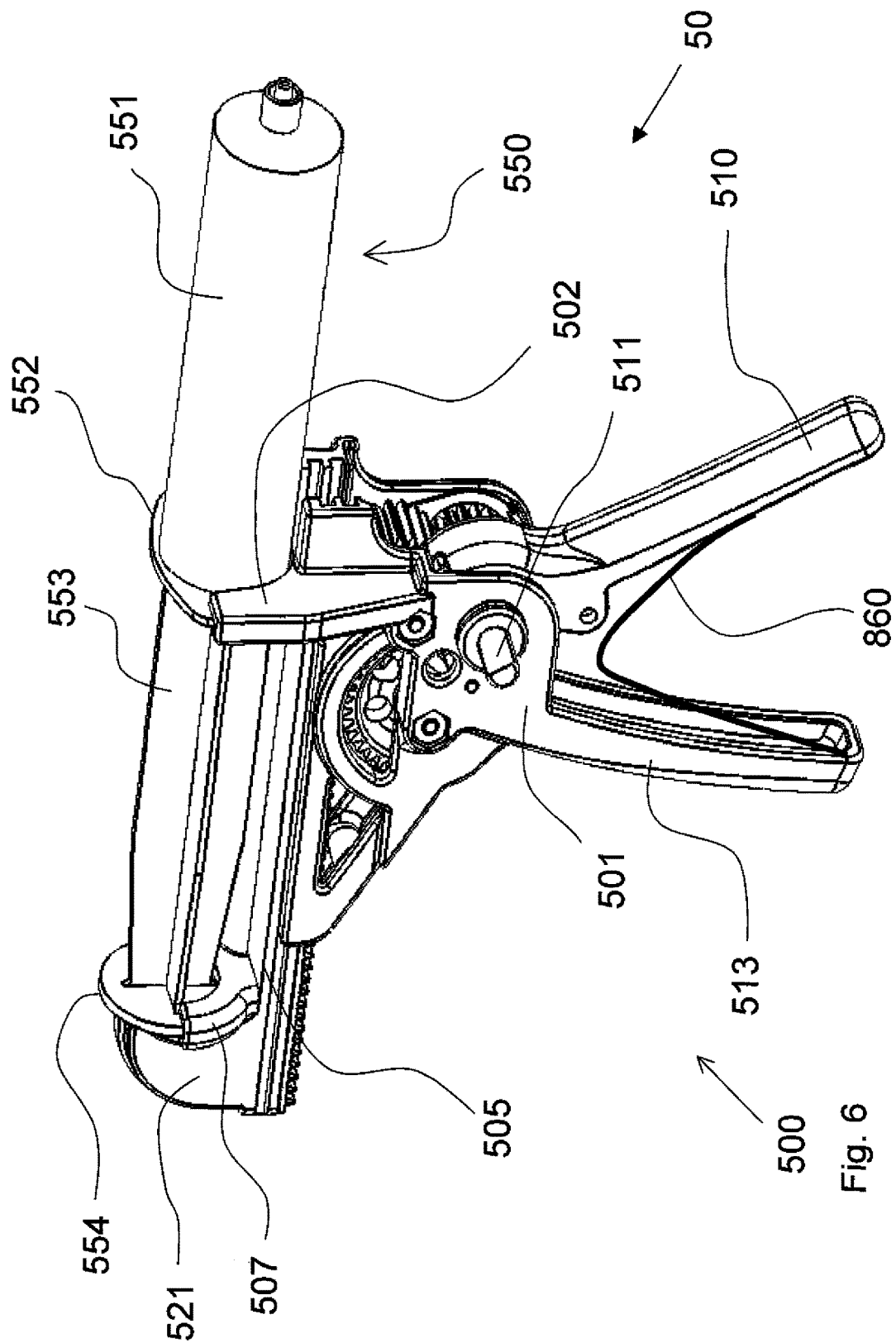
FIG. 6 is a perspective view of the embodiment of FIG. 5 coupled to a syringe.

Referring now to FIGS. 5 and 6 a preferred embodiment of a system 50 of the present invention that includes device 500 and syringe 550 coupled to device 500. System 50 can be used to both dispense and aspirate syringe contents (not shown). System 50 also easily switches between these two modes, advantageously with the same hand holding and actuating the device 500 if desired. FIG. 5 shows just the device 500 and FIG. 6 shows the device 500 with a typical syringe 550 mounted to it.

The device 500 has a main housing or chassis 513 made of two halves 501 and 520, each with a holder 502 and 523 respectively, which interface with the syringe body flange 552 of the syringe body 551. The two housing halves 501 and 520 are held together in this example with fasteners 519 and 522. Any number of fasteners could be used and alternative fastening methods could also be used such as snaps or adhesives for bonding the two halves. Housing half 501 also has guide rail 504 incorporated into it, and housing half 520 has guide rail 503 incorporated into it.

The carriage 505 is a component with a tooth pattern 509 incorporated into the bottom side along at least a portion of the length of carriage 505. Each side of carriage 505 has a channel (only one channel 506 can be seen in these views) that is along its entire length in this embodiment for purposes of illustration. The rear of the carriage 505 has a protruding structure 521 into which a retention feature or holder 507 is incorporated. The other end (not seen in the figures because the view is obstructed by the holder 502) does not have any protruding features in this embodiment, but may include such features in other embodiments. The plunger 553 of the syringe 550 has plunger flange 554, which interfaces with and is held by the carriage holder 507. The side channels (only 506 is seen in these views) of carriage 505 slidingly interface with mating rails 503 and 504. The carriage 505 also has a tooth pattern 509 to which the tooth pattern of the main drive gear 701 interfaces.

Referring now also to FIGS. 7 through 12, the device 500 has transmission assembly 700 which includes clutch system 531 and gear system 541. Clutch system 531 includes clutch 511, trigger 510, pawl holder plate 840, threaded ball plunger 831, pawls 801 and 802, and ratchet gear 800, which has a D-shape shaft opening 803. The clutch 511 has grooves 832 and 833, a shaft 532, and a clutch plate 705 that has holes 706. Pawl 801 has a shaft 804 and flex arm 805. Pawl 802 has a shaft 810 and flex arm 806. Gear system 541 includes gears 701, 702, 703, and 704, gear holder plate 841, and post plate 714 and spring 715 that comprise post assembly 712 for gear 702.

Depending upon which operation mode is selected, transmission assembly 700 can drive carriage 505 forward (first or dispense mode) or in reverse (second or aspiration mode). Forward mode presses plunger 553 into syringe body 551. This creates pressure that dispenses syringe contents. Reverse mode pulls plunger 553 out of syringe body 551. This creates aspiration that pulls contents into syringe 550 from an external source. Transmission assembly 700 includes clutch features to easily shift between forward and reverse modes on demand.

The transmission assembly 700 transmits the actuation force imparted by the user on the trigger 510 to the carriage 505. The transmission assembly 700 can change the rotational direction of the main drive gear 701 when the clutch 511 is shifted from one side to the other along its axis as indicated by the arrow 512. This unique transmission assembly 700 allows a user to move the plunger 553 of the syringe 550 in either direction (aspiration or dispensing) using the same trigger actuation of the trigger 510 towards the grip 513 of the chassis 501. The clutch 511 is designed and positioned in a way that a user can easily move it from side to side. Advantageously, this can be accomplished using a finger and/or thumb of the same hand that is holding and pulling the trigger 510 if desired. A torsion compression type spring 860 is incorporated between the inside of the trigger 510 and the housing 513 to keep the trigger 510 biased open (starting position) and away from the housing 513.

Figure 7:
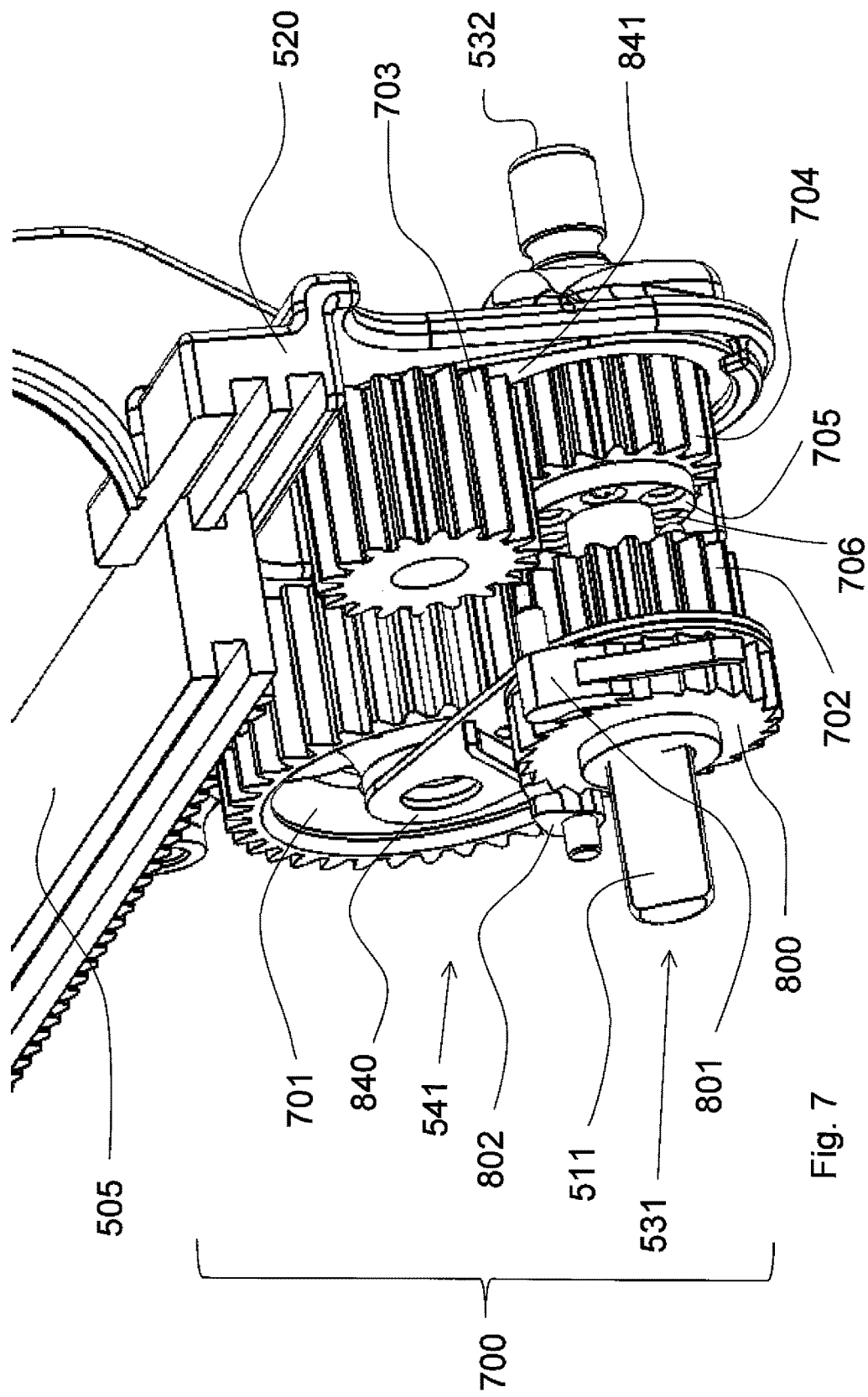
FIG. 7 is a perspective closeup view of select components of the transmission assembly within the device of FIG. 5.

Referring to FIG. 7, the transmission assembly 700 is shown in greater detail with just a portion of the housing half 520 shown. The teeth of the main gear 701 engage with the teeth 509 of the carriage 505. There are two gears 702 and 703 that directly engage with the main gear 701. Gear 703 also engages directly with gear 704. Clutch 511 causes one of gears 702 and 704 to be selectively engaged and driven by trigger actuation at one time. The clutch 511 has a clutch plate 705 with a number of holes 706 that are used to selectively engage the clutch 511 with one of gears 702 and 704. The shaft of the clutch 511 passes through the bore of gears 702 and 704, and through ratchet 800 (also called ratchet gear 800). As will be shown later, the bore of ratchet 800 has a key feature to rotationally lock it to the shaft of the clutch 511. The ratchet 800 engages with pawl 801 that is mounted to trigger 510 and pawl 802 that is mounted to housing 501.

Figure 8:
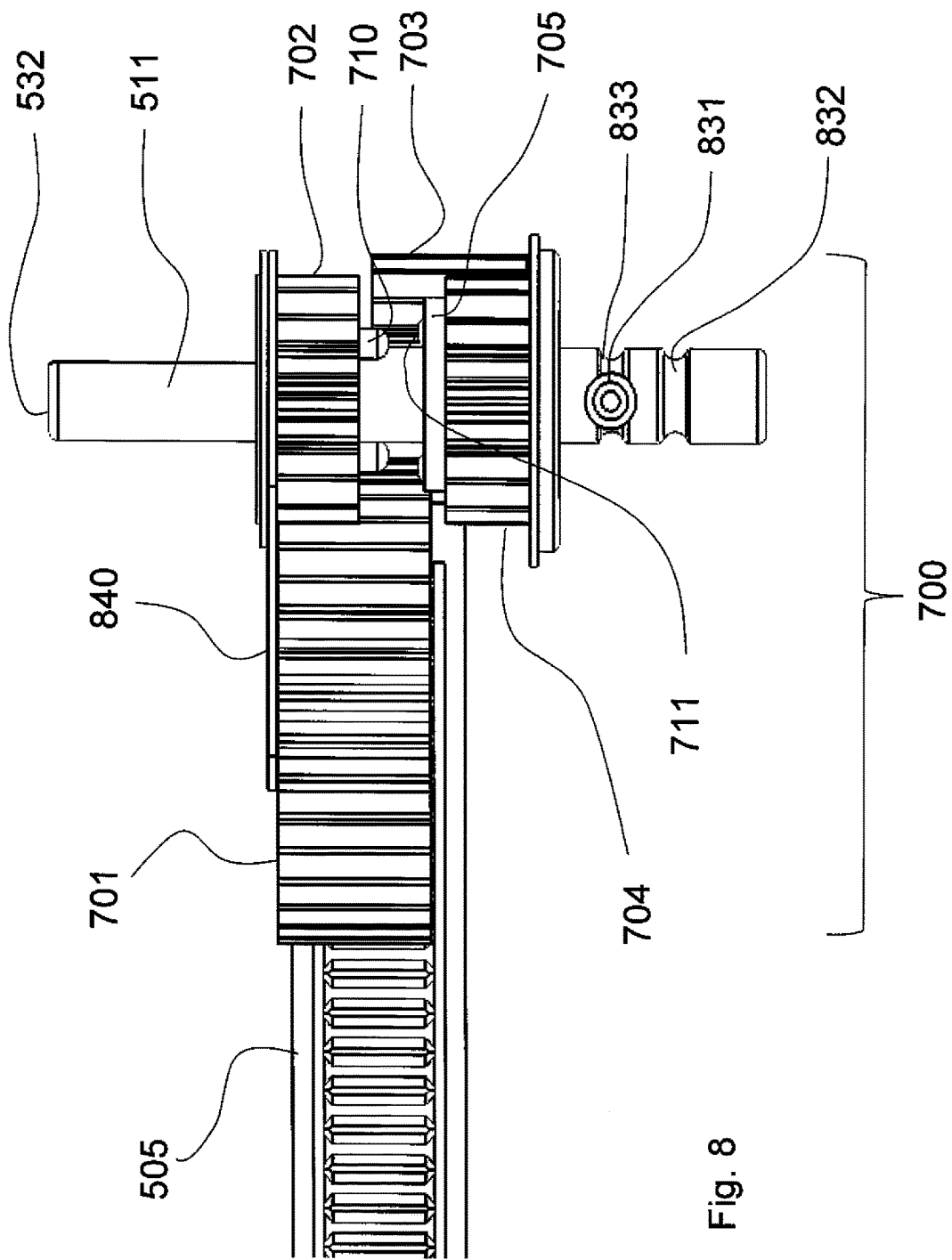
FIG. 8 is a bottom view of select components of FIG. 7.

Now referring also to FIG. 8, a bottom view of select components of the transmission assembly 700 is shown further illustrating the gears 702 and 703 that directly engage with the main gear 701. The gears 702 and 704 that also directly engage with the clutch 511 are shown. In this view, a plurality of posts 710 that extend from gear 702 and a plurality of posts 711 that extend from gear 704 are visible. These posts 710 and 711 selectively pass into the holes of the clutch plate 705 to rotationally lock the clutch plate 705 to the corresponding gear being engaged at the time. In FIGS. 7 and 8 the clutch 511 is shown engaged with gear 704, and posts 711 help secure clutch plate 705 to gear 704.

Figure 9:
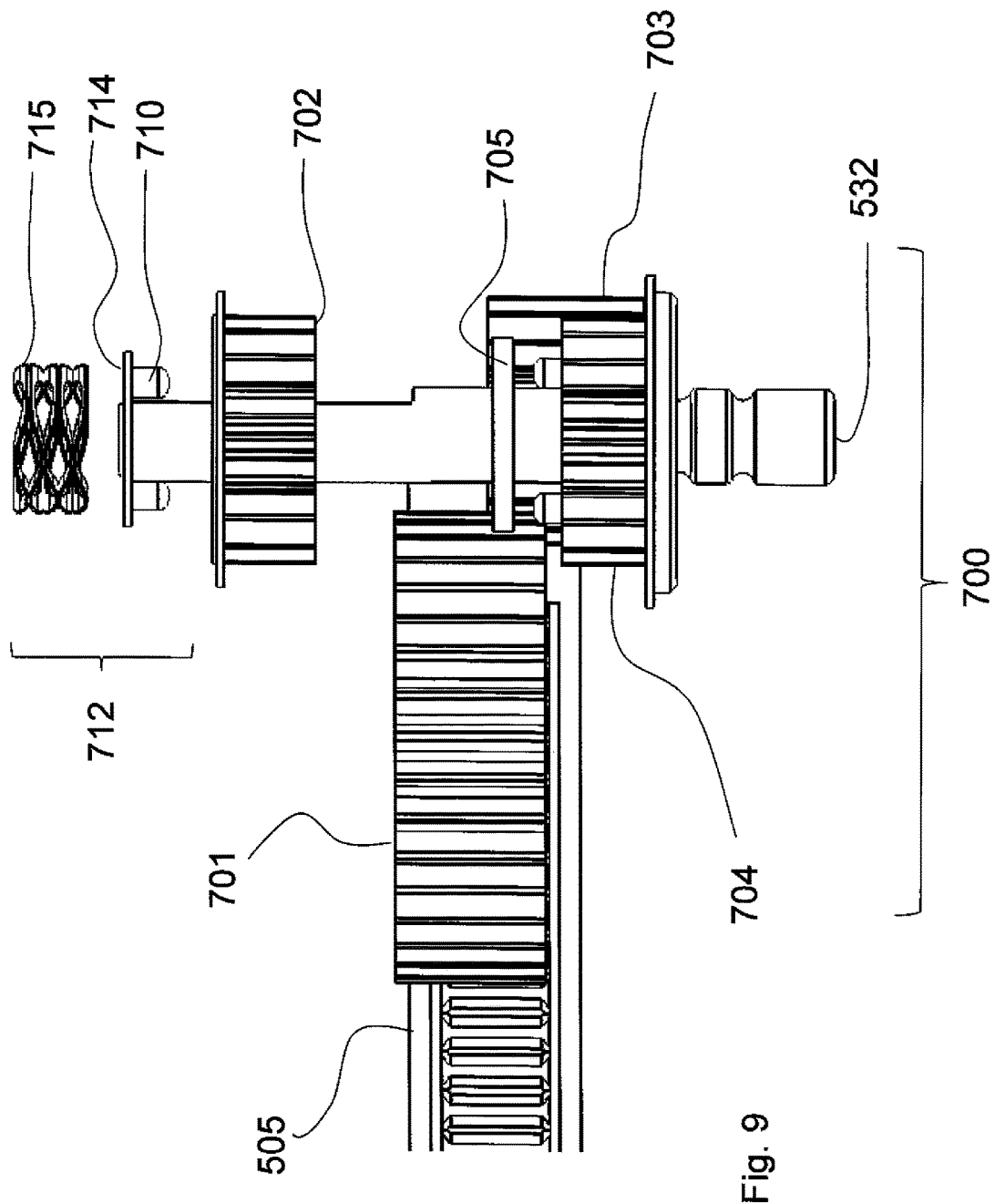
FIG. 9 is the same view as FIG. 8 except with the components inside one of the gears shown exploded from the main assembly.

FIG. 9 shows the same components as in FIG. 8 but with an exploded view of the post assembly portion 712 for gear 702. The posts 710 extend from a common plate 714 through which the shaft of the clutch 511 also passes. A spring 715, shown as a wavy spring, presses against the post plate 714 on one side and is held against housing 501 (not shown in this FIG.) to create a force to bias plate 714 toward clutch plate 705. The spring 715 also has the shaft of the clutch 511 pass through it. The spring 715 allows the posts 710 to be depressed by the clutch plate 705 if holes 706 do not happen to align with the posts 710 at the time the clutch 511 initially is shifted to engage with gear 702. A similar type of assembly as post assembly portion 712 exists for the other gear 704, so that clutch 511 can engage gear 704 to rotate gear 701, and hence drive carriage 505, in the other direction.

From these descriptions of the gear and clutch components of transmission assembly 700 illustrated in FIGS. 7 through 9, it can now be seen how, as the clutch 511 selectively engages gears of transmission assembly 700, trigger actuation can move the carriage 505 forward or backwards, which correspond to dispensing and aspirating the syringe, respectively. The forward or reverse mode is selected depending upon whether clutch 511 is engaged with gear 702 or 704.

Figure 10:
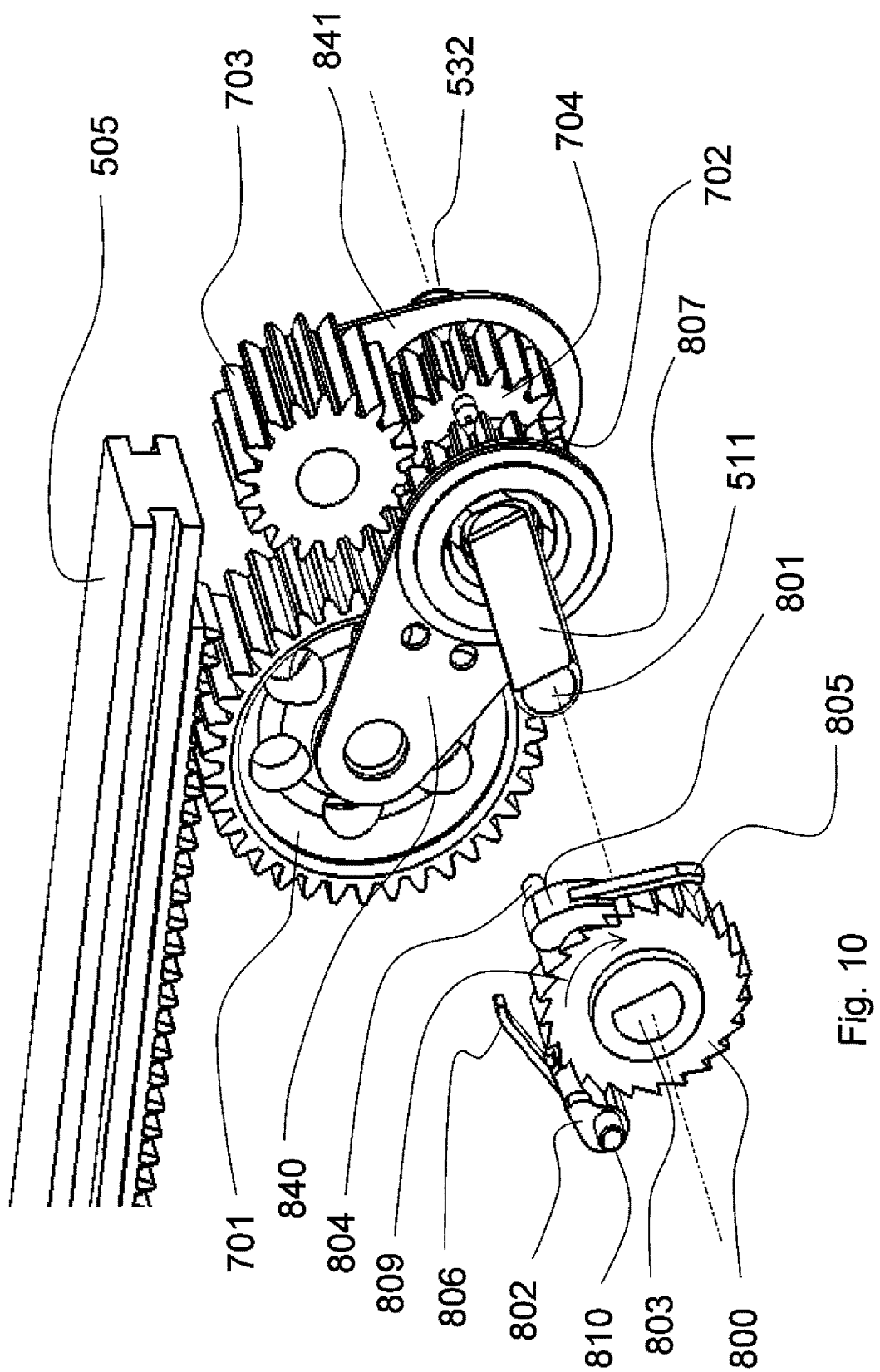
FIG. 10 is a perspective view of select transmission components from FIG. 7 with the ratchet and pawl components shown exploded from the main assembly.
Figure 11:
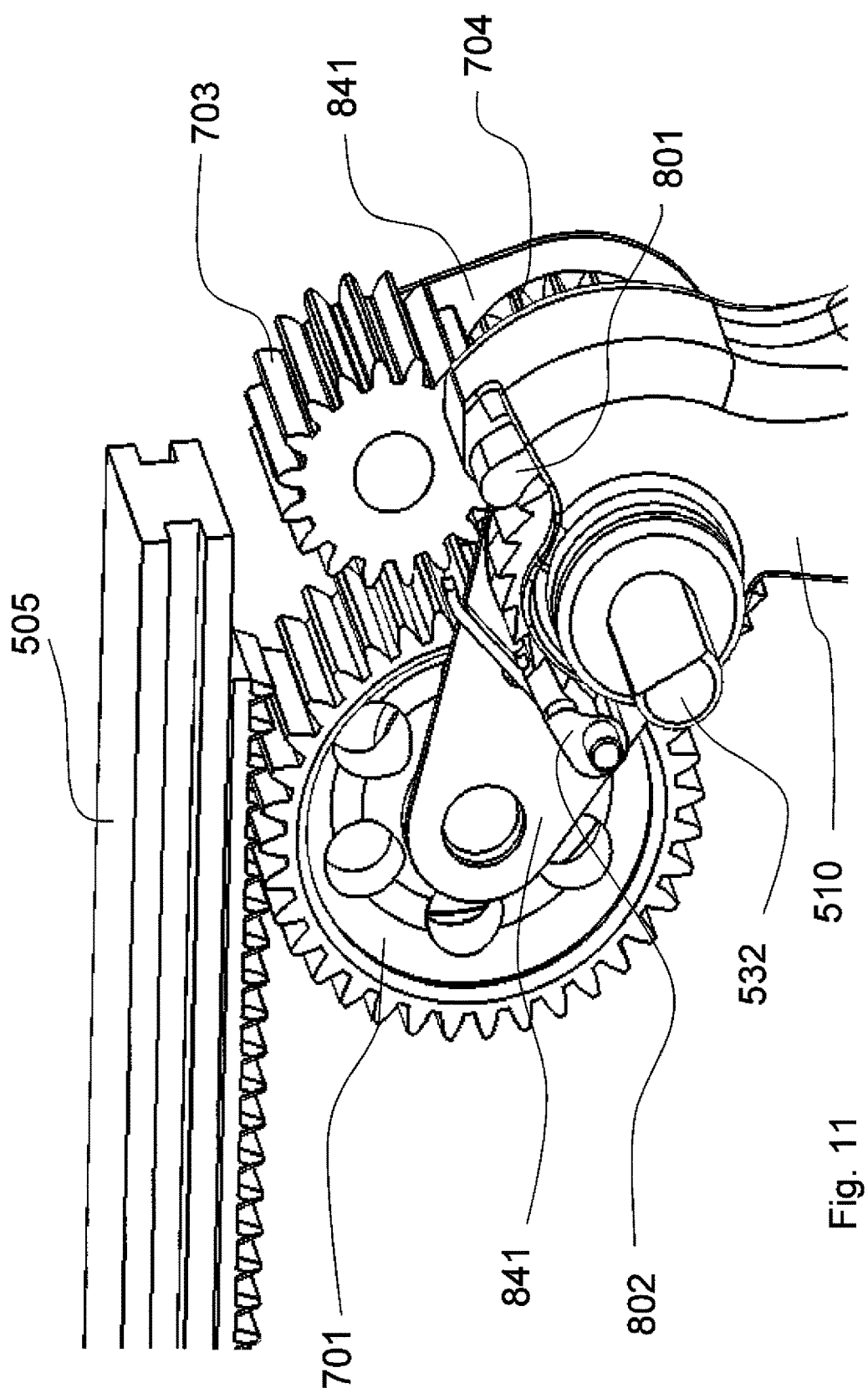
FIG. 11 is a perspective view of the components from FIG. 10 with a trigger attached.

Now referring to FIGS. 10 and 11, ratchet features are shown in more detail that describe how the ratchet 800 can be controlled using pawls 801 and 802 to only rotate ratchet 800 in one (forward) direction 809. For purposes of illustration, the ratchet 800 and pawls 801 and 802 are removed from the shaft of the clutch 511 in FIG. 10 to show how the D-shape bore 803 of the ratchet 800 interlocks with the mating D-shape portion 807 of the clutch 511. As a result of this interlock, any rotation of the ratchet 800 will cause a rotation of the shaft 532 of the clutch 511. The shaft 804 of pawl 801 engages with the trigger 510 and allows pawl 801 to pivot about the shaft 804. Flexure 805 of pawl 801 is flexed against the inside of the trigger 510. This creates a bias force that keeps the pawl 801 pressed against the ratchet 800 and yet allows pawl 801 to ride over the teeth of the rotating ratchet 800. The orientation of pawl 801 to the ratchet 800 is such that, as the trigger 510 is squeezed or pulled towards the grip 513 (FIGS. 5 and 6), the teeth of the pawl 801 interlock with the teeth of the ratchet 800 and cause the ratchet 800 to rotate in direction 809. This in turn causes the clutch 511 to rotate also in forward direction 809. When the trigger 510 is released, spring 860 shown in FIGS. 5 & 6 moves the trigger 510 back outward and it is during this motion that the pawl 801 rides over ratchet 800 teeth. In short, trigger 510 is operatively coupled to ratchet 800 via pawl 801 so that trigger actuation rotationally drives ratchet 800 forward in direction 809 and hence the shaft 532 of the clutch 511. This motion will cause the carriage 505 to move either forward or backward depending on which gear, 702 or 704, the clutch plate 705 selectively engages. The second pawl 802 prevents backward rotation (opposite 809) of ratchet 800.

Pawl 802 also has a shaft 810 that interfaces to the housing 513 shown in FIGS. 5 and 6, and allows pawl 802 to pivot about this shaft 810. Flexure 806 of pawl 802 is flexed against the inside of the housing 501 and creates a bias force that biases the pawl 802 against the ratchet 800 to help prevent backwards rotation (opposite 809) of ratchet 800, but yet allows pawl 802 to ride over the teeth of the rotating ratchet 800 to allow forward rotation in direction 809 of ratchet 800. The orientation of pawl 802 to the ratchet 800 is such that as the trigger 510 is squeezed or pulled towards the grip 513 (FIGS. 5 and 6), the teeth of the pawl 802 pass over the rotating ratchet 800. When the trigger 510 is released, spring 860 shown in FIGS. 5 and 6 push the trigger 510 back open, while the teeth of pawl 802 engage the ratchet 800 and prevent counter rotation (opposite 809) of the ratchet 800 and therefore motion of the transmission 700 and carriage 505. The two pawls 801 and 802 therefore only allow the ratchet 800 to rotate in one direction indicated by arrow 809 in FIG. 10 and help to prevent counter rotation. This is the main principle of these components and the design described herein is the preferred embodiment. Alternative embodiments are possible, and one example would be to make the pawls 801 and 802 completely rigid components and use a compression coil spring to provide the bias forces against the pawls.

Referring now to FIG. 12, select components of the device 500 shown in FIG. 1 are shown that show how the clutch 511 is held in the different positions. As has been described previously and shown in the figures in this preferred embodiment, the clutch 511 can move side to side so that its clutch plate 705 can selectively engage with gears 702 and 704. To ensure that the clutch 511 maintains the engaged position and provides a tactile feedback to the user that the engagement has been achieved, the housing 520 has a threaded hole 830 into which a standard type of threaded ball plunger 831 is placed. The ball plunger 831 interfaces with the shaft of the clutch 511 and extends into groove 832 when the clutch 511 is moved to engage with gear 704, and extends into groove 833 when the clutch 511 is moved in the other direction to engage with gear 702. The holding force provided by the ball plunger 831 prevents the clutch 511 from being pushed back as it is shifted against one of the gears 702 or 704 when the holes 706 of clutch plate 705 do not happen to align with the respective posts 710 or 711. When this happens, clutch plate 705 depresses the posts 710 or 711, which compresses the respective spring, for example spring 715 for posts 710, until the posts 710 or 711 align with the holes 706 of the clutch plate 705. This allows the posts 710 or 711 to extend into the holes 706 to create selective engagement between the clutch 511 and the respective gear 702 or 704.

The preferred embodiment presented in FIGS. 5 through 12 provides the features to allow a syringe to be dispensed and aspirated by moving a rotating clutch between two positions. The rotation of the shaft 532 of clutch 511 is always in one forward rotationally direction 809 in this illustrative embodiment. Shaft rotation occurs when a user pulls on trigger 510. The forward rotational direction 809 of clutch 511 is controlled by two pawls, 801 and 802, and ratchet gear 800. In the dispensing mode, the clutch 511 is moved to engage gear 704 that meshes with a second gear 703. Gear 703 in turn meshes with a final drive gear 701 that finally meshes with the teeth 509 of carriage 505. These series of gears are necessary so that the single forward rotational direction 809 of clutch 511 moves the carriage 511 forward to dispense contents of a syringe. In the aspiration mode, the clutch 511 is moved to engage gear 702, which meshes directly with the final drive gear 701 that again meshes with the teeth 509 of carriage 505. In this way, the single forward rotational direction 809 of clutch 511 can also move the carriage 511 backwards to aspirate material into the syringe. The single forward rotational direction 809 of clutch 511 is created by having a pawl 801 attached to trigger 510. This pawl 801 drives the rotation of ratchet gear 800 which is directly coupled to clutch 511. When the user releases trigger 510, the spring 860 pushes the trigger 510 back open to the starting trigger position for the user to squeeze the trigger 510 again. The second pawl 802 prevents the ratchet gear 800 and therefore the directly coupled clutch 511 from rotating in the backwards rotational direction (opposite direction 809) as the trigger 510 is pushed back to the starting trigger position.

An alternative embodiment of a different configuration is one in which an additional groove is provided, e.g., placed between the two 832 and 833 that are used to engage the gears 702 and 704. This additional groove would allow a neutral position where the clutch plate 705 does not engage either set of gears 702 or 704. In another preferred embodiment, an aspiration-only configuration is created by removing gears 704 and 703. In yet another preferred embodiment of a dispensing-only configuration, gear 702 is removed. In yet another preferred embodiment, the holder 502 and 523 can be detached from the housing halves 501 and 520, and connected to its own carriage that is connected by additional gears to the main gear 701 so that it moves in a direction opposite the carriage 505.

Advantageously, all of the components described herein can be made of non-ferrous materials which would make them suitable for use with MRI. The gears and housing in particular can also be cost effectively mass produced with injection molded plastic. Additionally, the relative sizes of the gears can be modified to generate different amounts of mechanical advantage for the force transmitted to the syringe by the trigger independently for each direction.

There are other applications where it is desired to have an ability to control motion of one or more components and the direction of such motion. Some additional applications involve controlling the motion of a fluid (e.g., to dispense, inject, or aspirate a fluid). Other applications involve controlling the position of one or more solid items. The present invention would be suitable to control actuation in multiple directions in a wide variety of such applications, including but not limited to the following exemplary uses.

General barrel plunger devices are conceptually similar to a fluid syringe but instead are configured so that a plunger is coupled to a solid object instead of a fluid. The principles of the present invention can be used to control actuation of the barrel plunger in both forward and reverse directions.

Some gripping devices control the movement of gases in order to grip and release items. For example, one device (known as a pooter device) allows small insects to be gently collected and held against an intake membrane such as a filter by steady intake of air through the membrane. The insect can be transferred to a container or other target by reversing operation and dispensing air or other gas through the membrane in the other direction. Vacuum gripping devices also are used in the microelectronic industry to hold workpieces. The principles of the present invention can be used to control actuation of pressurizing and aspirating components that cause the gas to provide gripping and releasing forces on demand.

Manual positioning systems can be used to control the position of items. An example is to control the height position of a chair via positive manual actuation to raise, lower, twist, or otherwise modify the chair configuration. Conventionally, gravity often is used to create a downward motion and a mechanical force would be used for upward motion. This conventional system would be replaced by a mechanism of the present invention that allows a user to control and move the chair in both directions via mechanical actuation, preferably without needing to stand up to raise or lower the height of the chair.

In another type of manual positioning system, one or more clamps are used to maintain the position of an object. Releasing the clamp allows the object to be re-positioned. A specific example includes the clamps that are used to position the legs of a camera tripod. The principles of the present invention can be used to control actuation of the clamps to both grip and release objects.

The present invention can also be used in toy water guns to control pressure and dispensing mechanisms. For instance, a transmission of the present invention can be used to actuate one or more components in a manner effective to aspirate water into the barrel of a toy water gun. The transmission mode can then be switched to actuate one or more components in a manner effective to dispense the water as a jet. Alternatively, the transmission of the present invention can be used to actuate one or more components in a manner effective to pressurize at least one chamber that to dispense the water. In some embodiments this could replace a typical two-handed pump action and allow pressurizing and dispensing to be accomplished with one hand.

The principles of the present invention also can be incorporated into other kinds of gripping tools such as clamps used to hold items together for gluing, welding, bolting, nailing, screwing, other fastening, or other treatment. Examples of these include clamps used in wood and metalworking. Other examples include golf shaft extractors that both grip a golf shaft and push against a club head to remove the head from the shaft. Transmissions of the present invention can be used to create the force that grips and releases the club and/or the force that pushes against the club head relative to the shaft.

The present invention has now been described with reference to figures of an exemplary embodiment thereof. The entire disclosure of any patent or patent application identified herein is hereby incorporated by reference for all purposes. The foregoing disclosure has been provided for clarity of understanding by those skilled in the art of injection and aspiration devices. No unnecessary limitations should be taken from the foregoing disclosure. It will be apparent to those skilled in the art that changes can be made in the exemplary embodiment described herein without departing from the scope of the present invention. Thus, the scope of the present invention should not be limited to the exemplary structures and methods described herein, but only by the structures and methods described by the language of the claims and the equivalents of those claimed structures and methods.

What is claimed is:

1. An actuation device to control motion of a workpiece, comprising:
   a) a slideable carriage coupled to the workpiece, said slideable carriage comprising gear teeth provided along at least a portion of the slideable carriage;
   b) a transmission coupled to the slideable carriage, said transmission comprising:
      i. a rotatably driven main drive gear coupled to the slideable carriage, said rotatably driven main drive gear being driveable in first and second rotational directions to cause corresponding first and second motions of the slideable carriage;
      ii. a rotatable shaft that is shiftable along an axis of shaft rotation;
      iii. a trigger coupled to the rotatable shaft such that trigger actuation causes the rotatable shaft to rotate in a shaft rotational direction;
      iv. a first selectively engaged and driven gear mounted on and selectively engaged with the rotatable shaft by a clutch system on the rotatable shaft, said first selectively engaged and driven gear being rotationally coupled to the rotatably driven main drive gear and selectively driven by a trigger actuation when selectively engaged with the rotatable shaft in a manner effective to cause rotation of the rotatably driven main drive gear in a first rotational direction when the first selectively engaged and driven gear is selectively engaged with and driven by rotation of the rotatable shaft;
      v. a second selectively engaged and driven gear mounted on and selectively engaged with the rotatable shaft by the clutch system on the rotatable shaft, said second selectively engaged and driven gear being rotationally coupled to the rotatably driven main drive gear and selectively driven by a trigger actuation when selectively engaged with the rotatable shaft in a manner effective to cause rotation of the rotatably driven main drive gear in a second rotational direction when the second selectively engaged and driven gear is selectively engaged with and driven by rotation of the rotatable shaft; and
         wherein the clutch system comprises a first configuration that causes the transmission to be in a first transmission mode that selectively engages the rotatable shaft with the first rotatably engaged and driven gear to drive the first selectively engaged and driven gear and a second configuration that causes the transmission to be in a second transmission mode that selectively engages the rotatable shaft with the second rotatably engaged and driven gear to drive the second selectively engaged and driven gear, and wherein the clutch system selectively engages the rotatable shaft to one of the first and second selectively engaged and driven gears on demand when the shaft is shifted along the axis of shaft rotation.

2. A method of actuating a syringe, comprising the steps of:
   a) providing an actuation device according to claim 1;
   b) loading the syringe into the actuation device;
   c) selecting a mode of actuation selected from dispensing and aspiration of the syringe;
   d) causing the actuation device to be in the desired mode of actuation; and
   e) actuating the actuation device to cause corresponding actuation of the syringe.

3. The actuation device of claim 1, wherein the workpiece comprises a syringe comprising a syringe body and a plunger, wherein the syringe body has a first open end and a second open end, and wherein the plunger fits into the first open end of the syringe body and is slideable to be moved into the syringe body toward the second open end and is slideable to be pulled from the syringe body away from the second end.

4. The actuation device of claim 3, wherein the slideable carriage holds the plunger and wherein the gear teeth provided along at least a portion of the slideable carriage engage the main drive gear such that rotational motion of the main drive gear applied to said gear teeth of the slideable carriage causes generally linear translation of the slideable carriage back and forth corresponding to the direction of an applied rotational motion; and wherein the actuation device further comprises a second portion that holds the syringe body such that the plunger held by the slideable carriage can be moved into and pulled from the syringe body held by the second portion as the slideable carriage translates.

5. The actuation device of claim 4, wherein the slideable carriage has a length-comprising sides and each side of the length of the slideable carriage comprises a channel, wherein the channel is capable of interfacing with mating rails of the second portion.

6. The actuation device of claim 4, wherein the carriage comprises a carriage holder that engages the plunger.

7. The actuation device of claim 1, wherein the clutch system further comprises a neutral configuration.

8. The actuation device of claim 1, wherein the rotatably driven main drive gear comprises teeth that engage with the gear teeth of the slideable carriage.

9. The actuation device of claim 1, wherein the first transmission mode causes movement of the slideable carriage in a first direction, and the second transmission mode causes movement of the slideable carriage in an opposite direction.

10. The syringe actuation device of claim 1, wherein a rotatably driven ratchet gear is mounted to the rotatable shaft and wherein the trigger is coupled to the rotatably driven ratchet gear in a manner such that trigger actuation rotates the rotatable shaft.

11. The actuation device of claim 1, wherein the clutch system comprises a clutch plate such that shifting the rotatable shaft causes the clutch plate to selective) engage one of the first and second selectively engaged and driven gears.

12. The actuation device of claim 11, wherein the clutch plate comprises a hole that can selectively engage a pin on one of the first and second selectively engaged and driven gears when the rotatable shaft is shifted.

13. The actuation device of claim 1 further comprising a ratchet gear mounted on the rotatable shaft such that rotation of the ratchet gear causes rotation of the rotatable shaft, a pawl coupled to the trigger and the ratchet gear in a manner such that actuation of the trigger causes the ratchet gear and the rotatable shaft to rotate, thereby causing the transmission to translate the slideable carriage.

* * * * *

UNITED STATES PATENT AND TRADEMARK OFFICE
CERTIFICATE OF CORRECTION

PATENT NO. : 10,099,244 B2
APPLICATION NO. : 14/419439
DATED : October 16, 2018
INVENTOR(S) : Pfahnl et al.

Page 1 of 1

It is certified that error appears in the above-identified patent and that said Letters Patent is hereby corrected as shown below:

In the Claims

Column 16
Line 52 "selective)" should be -- selectively --

Signed and Sealed this
Fourteenth Day of May, 2019

Andrei Iancu
*Director of the United States Patent and Trademark Office*